United States Patent [19]

Dexheimer et al.

[11] Patent Number: 5,141,662
[45] Date of Patent: Aug. 25, 1992

[54] HEAT TRANSFER FLUIDS COMPRISING OXYALKYLENATED POLYOLS

[76] Inventors: Edward M. Dexheimer, 26270 E. River Rd., Grosse Ile., Mich. 48138; Chung-Ji Tschang, 31 Hinterbergstrasse, 6702 Bad Duerkeim, Fed. Rep. of Germany

[21] Appl. No.: 719,865

[22] Filed: Jun. 24, 1991

Related U.S. Application Data

[63] Continuation-in-part of Ser. No. 480,313, Feb. 15, 1990, abandoned.

[51] Int. Cl.⁵ .................. C09K 5/00; C10M 105/08; C10M 105/50
[52] U.S. Cl. .................. 252/73; 252/51.5 A; 252/51.5 R; 252/52 R; 252/67; 252/68; 252/74; 252/75; 252/77; 252/79
[58] Field of Search .............. 252/73, 74, 75, 77, 252/79, 51.5 A, 51.5 R, 49, 52, 67, 68

[56] References Cited

U.S. PATENT DOCUMENTS

| | | | |
|---|---|---|---|
| 2,902,478 | 9/1959 | Anderson et al. | 252/73 |
| 4,332,936 | 6/1982 | Nodelman | 536/120 |
| 4,380,502 | 4/1983 | Müller et al. | 536/18.3 |
| 4,617,984 | 10/1986 | Harding et al. | 252/73 |
| 4,622,160 | 11/1986 | Buske et al. | 252/73 |
| 4,624,299 | 11/1986 | Harding et al. | 252/73 |
| 4,770,804 | 9/1988 | Hentschel et al. | 252/77 |
| 4,820,810 | 4/1989 | Klein et al. | 536/41 |
| 5,002,678 | 3/1991 | Vanover et al. | 252/68 |

OTHER PUBLICATIONS

LeMaistre, J. W. et al., "The Reaction of Sucrose with Ethylene Oxide", *J. Org. Chem.;* 13, 1948 (782-85).

*Primary Examiner*—Paul Lieberman
*Assistant Examiner*—William S. Parks

[57] ABSTRACT

Heat transfer fluids having high thermal stability are comprised of certain polyether polyols. The heat transfer fluids are used as solder fluids and in metal quenching and tempering baths, in solder reflow or alloying baths, and as lubricants for vulcanizing rubber hose.

5 Claims, No Drawings

HEAT TRANSFER FLUIDS COMPRISING OXYALKYLENATED POLYOLS

This is a continuation-in-part of copending application(s) Ser. No. 07/480,313 filed on Feb. 15, 1990, now abandoned.

FIELD OF THE INVENTION

The present invention relates to heat transfer fluids having high thermal stability comprised of certain polyether polyols, as well as to the use of certain polyether polyols as heat transfer or solder fluids in metal quenching and tempering baths and in solder reflow or alloying baths, and as lubricants for vulcanizing rubber hose.

1. Background of the Invention

Today, most industrial processes are designed to conserve or reuse raw materials and to minimize heat loss. For this purpose, a wide variety of heat transfer fluids are available.

For low temperature heat, the fluorochlorohydrocarbons serve as efficient means of heat transfer. For moderate temperatures, aqueous systems, generally containing suitable corrosion inhibitors are in general use, while at moderately elevated temperatures various glycols such as ethylene glycol, propylene glycol and their low molecular weight oligomers such as diethylene glycol have proven useful and cost effective. For higher temperature applications, however, especially those above 350° F. (176° C.), few satisfactory heat transfer fluids are available, and those that are available suffer from serious drawbacks.

Polyhalogenated hydrocarbons such as polychlorinated and polybrominated biphenyls and biphenyloxides have been utilized as high temperature heat transfer fluids. These fluids are particularly useful where resistance to flammability is important. However, these fluids are expensive, at least potentially carcinogenic, and especially deleterious to the environment. They cannot be utilized in open systems due to the possibility of inhalation. Moreover, these compounds, because of their high halogen content, may cause corrosion problems with certain metals such as the non-stainless steels, copper, lead, and tin at the elevated temperatures at which they are used. Furthermore, in many applications water solubility is essential and these types of fluid are virtually insoluble in water.

Low molecular weight oligomeric polyoxyalkylene glycols are water soluble and can be utilized to some extent in higher temperature applications in closed systems, but tend over long periods of time to resinify and deposit large quantities of tar or sludge. Furthermore, they cannot be utilized in open systems due to their tendency to volatilize and to smoke or fume. As a function of molecular degradation, flashpoint can decrease so that a safe use of oligomeric polyoxyalkylene glycols is not guaranteed.

High molecular weight polyoxyalkylene glycols have been proposed as high temperature heat transfer fluids due to their lower volatility and greater thermal stability, for example, in U.S. Pat. No. 3,054,174. Polymers of this class, such as the high molecular weight polyoxyethylene glycols, have achieved some success commercially. However, they are still much too volatile for many high temperature uses such as reflow of low temperature alloys. Furthermore, they tend to fume excessively, and, although water soluble themselves, tend to deposit a varnish type residue which is difficult, if not impossible, to remove by standard techniques such as water washing. An additional drawback is that the more stable, higher molecular weight products are solids at room temperature and thus present handling problems which render them totally unacceptable in some industries.

Polyoxyethylene-polyoxypropylene block copolymers derived from bisphenol A have been proposed for limited use in a high temperature application in U.S. Pat. No. 4,360,144. These bisphenol A initiated copolymers are suggested for use in wave soldering machines where their function is to lower the solder surface tension and minimize surface oxidation of the molten solder. The thermal stability of these prior art polyethers decreased as the polyoxyethylene content increased. However, even in this special application, these polyethylene-polyoxypropylene copolymers have not been able to displace the more economical nonylphenol oxyethylates. Both the nonylphenol/oxyethylenates and the products of U.S. Pat. No. 4,360,144 have the further drawback of producing sludge during their use, especially when used in bulk. Furthermore, their high viscosity when mixed with water make it difficult to remove them completely from substrates by commercial rinsing techniques.

2. Description of the Related Art

McEntire et. al., U.S. Pat. No. 4,547,304 discloses a solder fusing fluid for use in the high temperature cleaning of printed circuit boards and the like comprising an alkylene oxide adduct and a primary amine or an ethoxylate thereof which is water soluble and stable at elevated temperatures. The alkylene oxide adduct may comprise ethylene oxide or a mixture of ethylene oxide and propylene oxide. The alkylene oxide is mixed with an initiator which comprises an alcohol having from about 1-20 carbon atoms. Included within this grouping as an initiator are triols such as glycerol. An oxidation inhibitor such as an alkylphenol or an arylamine or diarylamine is included. Primary amines are also included as other components of the solder fluid.

Nodelman, U.S. Pat. No. 4,332,936 discloses a method for making polyether polyols from solid initiator compounds containing 4 to 8 hydroxyl groups. The method includes dissolving the solid initiator compound in a solvent such as dimethyl formamide prior to alkoxylation. The method is particularly useful in making high functional sucrose-based polyether polyols which can be readily processed at moderate temperatures and give low color products. These polyols are particularly suited for the production of rigid polyurethane foams. There is no showing of using the polyether polyols of Nodelman as a high temperature solder fluid.

Klein et. al., U.S. Pat. No. 4,820,810 discloses urea catalysts useful in the preparation of sucrose polyols which are in turn useful in making rigid polyurethane foams. The polyols are prepared by reacting a polyhydric initiator or mixtures thereof with one or more alkylene oxides in the presence of a catalytically effective amount of urea. The preferred polyhydric initiator is sucrose but other initiators such as glycerine and sorbitol may also be utilized either alone or in mixtures with sucrose. The alkylene oxide is reacted with the sucrose in a mole ratio of alkylene oxide to sucrose ranging from about 8:1 to about 20:1. The sucrose is reacted with propylene oxide or ethylene oxide and urea serves as a catalyst and coinitiator in the alkoxylation reaction. Tertiary amine co-catalysts may also be present. The resulting composition is utilized in the manufacture of rigid polyurethane foams.

Muller et. al., U.S. Pat. No. 4,380,502 discloses polyether polyols made by alkoxylating a mixture which is from 20-80 weight percent sucrose and 20-80 weight percent formitol. The product polyether polyols have an average hydroxyl functionality of at least 3 and a hydroxyl number of from 28 to 1000. The polyether polyols are particularly useful in the formation of rigid polyurethane foams.

Dexheimer, U.S. Pat. No. 4,699,727 relates to thermally stable heat transfer fluids which are epoxyoxyethylene polymers initiated with bisphenols. Oxyalkylenation is accomplished by utilizing ethylene oxide, or ethylene oxide and a very minor amount of a higher C3-C4 alkylene oxide such as propylene oxide or butylene oxide.

OBJECTS OF THE INVENTION

It is an object of the present invention to provide thermally stable heat transfer fluids comprised of certain polyether polyols.

It is a further object of the invention to provide for the use of polyether polyols as heat transfer or solder fluids in metal quenching and tempering baths and in solder reflow or alloying baths, and as lubricants for vulcanizing rubber hose.

It is another object of the invention to provide a method of heat transfer utilizing the heat transfer fluids of the invention.

SUMMARY OF THE INVENTION

These and other objects of the invention are achieved by providing thermally stable heat transfer fluids comprised of certain polyether polyols. The present invention also relates to the use of certain polyether polyols as heat transfer or solder fluids in metal quenching and tempering baths and in solder reflow or alloying baths, and as lubricants for vulcanizing rubber hose.

Also provided as part of the invention is a method of heat transfer which involves contacting an object with the heat transfer fluid of the invention for a period of time sufficient to effect heat transfer between the fluid and the object.

The heat transfer fluids are thermally stable and thus do not volatilize or fume appreciably at high temperatures within the range of at least about 170 to 220 degrees C. In addition, they are substantially soluble in water and of low viscosity so that they are easily removed by rinsing, and do not tend to deposit sludge nor resinify to varnish-like substances. These heat transfer fluids and methods place little or no stress on the environment, and may be utilized in either open or closed systems.

DETAILED DESCRIPTION OF THE PREFERRED EMBODIMENTS

The polyether polyols useful in the heat transfer fluids and methods of the invention are typically prepared by reacting one or more low molecular weight alkylene oxides with one or more saccharides, or mixtures thereof. The reaction products typically have molecular weights in the range of from about 700 to 1800. The reaction processes are well known in the art, and are disclosed for example, in U.S. Pat. Nos. 3,085,085 and 2,902,478. The saccharides are reacted with about 1 to 6 moles of the alkylene oxide per saccharide hydroxyl group.

The alkylene oxides useful in the invention are preferably ethylene oxide or propylene oxide, and mixtures thereof. Other suitable oxyalkylenates include 1,2- and 2,3 butylene oxide, isobutylene oxide, butadiene monoxide, styrene oxide and the like, as well as mixtures thereof. Ethylene oxide is particularly preferred, and propylene oxide may be utilized where hydrophobicity is required.

The saccharides useful in the invention include the monosaccharides and disaccharides such as, for example, sucrose, sorbitol and dextrose, as well as mixtures thereof. The disaccharides are preferred. Of these, sorbitol is particularly preferred, as well as sucrose and mixtures of sorbitol and sucrose. When mixtures of sorbitol and sucrose are utilized, the sorbitol is preferably present in the sorbitol/sucrose mixture in an amount of from about 25 to 50 weight percent.

Based on the foregoing, the heat transfer fluid according to a particularly preferred embodiment of the invention has as a major component the polyether sucrose oxyethylenate. Sucrose oxyethylenate is the reaction product of sucrose and ethylene oxide. Other preferred polyethers include sorbitol oxyethylenate and sucrose/sorbitol oxypropylenate.

The thermally stable heat transfer fluids of the subject invention may be formulated with a wide variety of additives to enable performance of specific functions while maintaining their excellent thermal stability. In closed systems exposed to metal surfaces, for example, a variety of corrosion inhibitors including both those operating in the liquid phase and vapor phase, i.e., morpholine, may be added. Various organic amines, carboxylic acids, and carboxylic acid amides may be used for such functions. These various corrosion inhibitors are well known to those skilled in the art.

Antioxidants such as hindered phenols, phenothiazines and the like may also be added if appreciable amounts of entrained air are expected to be contained within the system. In open systems, the presence of antioxidants is especially desirable. Examples of suitable antioxidants are the polymeric hindered phenols such as IRGANOX ® 1010, available from Ciba-Geigy Corporation, Greensboro, N.C. Also suitable are stabilizers produced via reaction in the presence of a Friedel-Crafts type catalyst of dicyclopentadiene and p-cresol followed by further reaction with isobutylene. The preparation of such inhibitors is described in U.S. Pat. No. 3,751,375, for example. One such stabilizer is available from the Goodyear Tire and Rubber Company, Akron, Ohio, under the trade name WINGSTAY ® L. Conventional stabilizers such as butylated hydroxyanisole (BHA) and butylated hydroxytoluene (BHT) may also be utilized. Another even more preferred antioxidant is phenothiazine. Antioxidants are preferably present in amounts of from about 0.05 percent to 5 percent by weight, preferably from about 0.1 to 1.5 percent by weight, and most preferably from about 0.3 to 0.8 percent by weight.

Other additives may be added as the situation demands. For example, if the heat transfer fluids are to be utilized in solder reflow baths or as a combination heat transfer and oxidation prevention layer in stationary solder pots, it may be advisable to add from 1 percent to 10 percent by weight of a $C_9C_{22}$ long chain carboxylic acid, for example, oleic acid. In those applications where the prevention of foam is essential, defoamers may be added. Suitable defoamers are the well known silicone oils and high polyoxypropylene content polyoxyalkylene surfactants. Examples of the latter are PLURONIC® L-61 and L-62 polyoxyalkylene polyethers.

The thermally stable heat transfer fluids of the present invention may also be used in conjunction with other polyoxyalkylene fluids, or with other functional fluids such as neopentyl glycol diesters. However, the amounts of such other fluids must generally be minimized in order to maintain the superior thermal stability of the heat transfer fluids of the subject invention. When nonylphenol oxyethylenates are used, for example, generally less than 20 percent, preferably less than 10 percent of such nonylphenol oxyethylenates should be used.

PREPARATIVE EXAMPLE

The following example sets forth a method of preparation of sucrose polyether. This example is provided by way of illustration, and should in no way be construed as limiting the scope of the invention:

To a prepared one gallon autoclave was added 513 g sucrose, 128 g water, and 9 g 45% aqueous KOH. Ethylene oxide (600g) was added at 105 degrees C. When addition was complete, the product was vacuum stripped at 110 degrees C and 1 mm Hg. Addition of ethylene oxide was continued until a total of 1584 g was added. The product was vacuum stripped to remove volatile impurities and neutralized with 4.5 g acetic acid.

The heat transfer fluids of the present invention will find application as heat transfer or solder fluids in, for example, metal quenching and tempering baths and in solder reflow or alloying baths, and as lubricants for vulcanizing rubber hose.

The heat transfer fluids according to the invention may be utilized in wave soldering and PCB fabrication to reduce surface tension, eliminate dross formation and as a heat transfer medium in reflowing plated circuit boards and hot tinning bare copper boards. These fluids will find at least two major applications in the circuit board manufacturing process. In the soldering of assembled boards the polyether polyols may be used as an "oil-intermix" in the solder wave of a wave soldering machine to keep the surface oxide free and to reduce the surface tension of the solder deposited on the circuit board. These polyols may also be used on wave soldering machines without the "intermix" feature and on static solder pots as a "dross blanket" to avoid solder oxidization which results in dross formation. In these applications, the heat transfer fluids may be referred to as "wave oil".

In fabrication the circuit board heat transfer fluids are used primarily as a heat transfer medium to reflow the tin-lead deposit over copper to form an intermetallic bond between the two metals and provide a highly solderable fused solder finish. The printed circuit board is typically on some type of a conveyor belt and the connections (e.g. diodes and transistors) to be soldered are exposed so that the heat transfer fluid acts as an interface between the solder and the board. The heat transfer fluid "transfers" the heat necessary for soldering the connections.

In hot tinning copper circuit boards hot fluid is sprayed onto the hot soldered board to wipe off (squeegee) any excess solder to form a smooth, even coating of solder on all copper surfaces. Oils used in the fabricating process are usually referred to as "reflow fluids".

The heat transfer fluids according to the invention can furthermore withstand the high temperature of the solder without degradation. These fluids are also highly water soluble since they should be completely washed off their contacts after use.

Similar uses as set forth above for the heat transfer fluids according to the invention may occur to those skilled in the art and are certainly within the scope of the invention.

The unexpectedly high thermal stability of oxyethylenated saccharides according to various embodiments of the invention is even higher than the oxyethylenated polyamine disclosed in McEntire '304 (77% vs. 68% residue after 4 hours). This is surprising because the saccharide starting materials are expected to exhibit poor thermal stability and propylene oxide lowers the thermal stability relative to ethylene oxide.

The following comparative examples in Table I are offered to further illustrate various aspects of the invention. Those skilled in the art will recognize they are not to be construed as limiting the scope thereof.

Table I compares examples of this invention with a commercial high temperature fluid (Iconol NP-10) embodying the prior art, and an experimental high temperature fluid. The instant invention is superior to the commercial fluid. Although both sorbitol and dipentaerythritol are hexols, sorbitol as an initiator provides twice the thermal stability, demonstrating that stability is not simply due to a highly branched structure or large number of hydroxyl groups.

TABLE I
THERMAL STABILITY OF POLYETHERS

| POLYETHER | PAN TEST* RESIDUES (%) | |
|---|---|---|
| | 1 HR. | 4 HRS. |
| 2200 MW OXYALKYLENATE OF DIPENTAERYTHRITOL | 46 | 24 |
| SUCROSE/SORBITOL OXYPROPYLENATE | 86 | 77 |
| SUCROSE + 24 EO | 91 | 66 |
| SORBITOL OXYALKYLENATE EO5907 | 90 | 78 |
| ICONOL NP-10** | 84 | 50 |

*RESIDUE FROM 3.0 g SAMPLES IN 240° C. OVEN
**COMMERCIAL SOLDER FLUID

While the invention has been described in detail in each of its several embodiments, it is expected that certain modifications may occur to those skilled in the art without departing from the spirit and scope of the invention as set forth in the following claims:

What is claimed is:

1. A method of heat transfer in high temperature applications which comprises contacting an object with a heat transfer fluid for a time sufficient to effect heat transfer between said object and said fluid, said fluid being comprised of a saccharide oxyalkylate selected from the group consisting of sucrose oxyethylate and mixtures of sucrose oxypropylate and sorbitol oxypropylate.

2. The method of claim 1, wherein said high temperature applications are selected from the group consisting of metal quenching, tempering baths, solder reflow and alloying baths, and lubricants for vulcanizing rubber hose.

3. The method of claim 1, wherein said sucrose oxyethylate comprises 24 ethylene oxide groups per sucrose molecule.

4. The method of claim 1, wherein said mixtures of sucrose oxypropylate and sorbitol propylate comprises mixtures of a sucrose and sorbitol mixture having sorbitol in an amount of from about 25 to 50 weight percent.

5. The method of claim 1, wherein said high temperature applications are in the range of from about 170 to 220 degrees C.

* * * * *